(12) United States Patent
Festa et al.

(10) Patent No.: US 10,045,990 B2
(45) Date of Patent: Aug. 14, 2018

(54) ERBB4 INHIBITORS AND METHODS OF USE THEREOF

(71) Applicant: Arizona Board of Regents on behalf of Arizona State University, Scottsdale, AZ (US)

(72) Inventors: Fernanda Festa, North Wales, PA (US); Joshua Labaer, Chandler, AZ (US); Jin Park, Phoenix, AZ (US); Femina Rauf, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/555,241

(22) PCT Filed: Mar. 2, 2016

(86) PCT No.: PCT/US2016/020422
§ 371 (c)(1),
(2) Date: Sep. 1, 2017

(87) PCT Pub. No.: WO2016/141044
PCT Pub. Date: Sep. 9, 2016

(65) Prior Publication Data
US 2018/0050038 A1    Feb. 22, 2018

Related U.S. Application Data

(60) Provisional application No. 62/128,239, filed on Mar. 4, 2015.

(51) Int. Cl.
*A61K 31/519* (2006.01)
*A61K 31/517* (2006.01)

(52) U.S. Cl.
CPC .......... *A61K 31/519* (2013.01); *A61K 31/517* (2013.01)

(58) Field of Classification Search
None
See application file for complete search history.

(56) References Cited

U.S. PATENT DOCUMENTS

| | | |
|---|---|---|
| 7,514,444 B2 | 4/2009 | Honigberg et al. |
| 7,718,662 B1 | 5/2010 | Chen et al. |
| 2011/0039868 A1 | 2/2011 | Honigberg et al. |
| 2011/0281322 A1 | 11/2011 | Honigberg et al. |

FOREIGN PATENT DOCUMENTS

| | | |
|---|---|---|
| WO | 2015023703 A1 | 2/2015 |
| WO | 2016071770 A2 | 5/2016 |

OTHER PUBLICATIONS

Gao et al., Journal of the National Cancer Institute (2014), 106(9), pp. dju204/1-dju204/4.*
Anastas, J. et al., "WNT signalling pathways as therapeutic targets in cancer", Nature Reviews Cancer, Jan. 2013 available online Dec. 2012), 13(1), pp. 11-26.
Anderson, K. et al., "Protein Microarray Signature of Autoantibody Biomarkers for the Early Detection of Breast Cancer", Journal of Proteome Research, Jan. 2011 (available online Oct. 2010), 10(1), pp. 85-96.
Arend, R. et al., "The Wnt/β-catenin pathway in ovarian cancer a review", Gynecologic Oncology, Dec. 2013 available Oct. 2013), 131(3), pp 772-779.
Arteaga, C. et al., "ERBB receptors: from oncogene discovery to basic science to mechanism-based cancer therapeutics", Cancer Cell, Mar. 2014, 25(3), pp. 282-303.
Balasubramanian, S. et al., "Mutational Analysis of Patients with Primary Resistance to Single-Agent Ibrutinib in Relapsed or Refractory Mantle Cell Lymphoma (MCL)", Blood, Dec. 2014, 124(21), pp. 78, abstract from 56th ASH Annual Meeting and Exposition, San Francisco, obtained online on Feb 15, 2018, <http://www.bloodjournal.org/content/124/21/78>.
Barretina, J. et al., "The Cancer Cell Line Encyclopedia enables predictive modelling of anticancer drug sensitivity", Nature, Mar. 2012, 483(7391), pp. 603-607.
Berglof, A. et al., "Targets for Ibrutinib Beyond B Cell Malignancies", Scandinavian Journal of Immunology, Sep. 2015 (available online Aug. 2015), 82(3), pp 208-217.
Bian, X. et al., "Tracking the Antibody Immunome in Type 1 Diabetes Using Protein Arrays", Journal of Proteome Research, Jan. 2017 (available online Oct. 2016), 16, pp. 195-203.
Blanke, C. et al., "Long-term results from a randomized phase II trial of standard—versus higher-dose imatinib mesylate for patients with unresectable or metastatic gastrointestinal stromal tumors expressing KIT", Journal of Clinical Oncology, Feb. 2008, 26(4), pp. 620-625.
Carpenter, G., "ErbB-4: mechanism of action and biology", Experimental Cell Research, Mar. 2003 (available online Feb. 2003), 284, pp. 66-77.
Chong, K. et al., "Wnt pathway activation and ABCB1 expression account for attenuation of Proteasome inhibitor-mediated apoptosis in multidrug-resistant cancer cells", Cancer Biology & Therapy, Jan. 2015, 16(1), pp. 149-159.
Cronauer, M. et al., "Effects of WNT/β-catenin pathway activation on signaling through T-cell factor and androgen receptor in prostate cancer cell lines", International Journal of Oncology, Apr. 2005, 26(4), pp. 1033-1040.
Davies, S. et al., "High incidence of ErbB3, ErbB4, and MET expression in ovarian cancer", International Journal of Gynecological Pathology, Jul. 2014, 33(4), pp. 402-410.
Demetri, G. et al., "Efficacy and safety of imatinib mesylate in advanced gastrointestinal stromal tumors", New England Journal of Medicine, Aug. 2002, 347(7), pp. 472-480.
Drier, Y. et al., "Pathway-based personalized analysis of cancer", PNAS, Apr. 2013, 110(16), pp. 6388-6393.

(Continued)

*Primary Examiner* — Brian J Davis
(74) *Attorney, Agent, or Firm* — Quarles & Brady LLP

(57) ABSTRACT

Disclosed herein are methods of treating diseases that exhibit over-activation of the ERBB4 pathway, such as breast cancer and lung cancer. The method comprises administering to a subject having a disease that exhibits over-activation of the ERBB4 pathway and a gene expression profile consistent with an ERBB4-sensitive profile a therapeutically effective amount of an ERBB4 inhibitor, wherein the disease is effectively treated. Gene expression profiles of ERBB4-sensitive cells and microarrays suitable for protein-tyrosine kinases are also provided.

9 Claims, 12 Drawing Sheets

(56) References Cited

OTHER PUBLICATIONS

Elias, L. et al., "BTK inhibitor ibrutinib inhibits breast cancer growth by inhibiting ErbB2 kinase", Molecular Cancer Therapeutics, Nov. 2013, vol. 12, suppl. 11, abstract C258.
Festa, F. et al., "Robust microarray production of freshly expressed proteins in a human milieu", Proteomics Clinical Applications, Jun. 2013 (available online May 2013), 7(5-6), pp. 372-377.
Gilmour, L. et al., "Expression of erbB-4/HER-4 Growth Factor Receptor Isoforms in Ovarian Cancer", Cancer Research, Mar. 2001, 61(5), pp. 2169-2176.
Grabinski, N. et al., "Ibrutinib (ImbruvicaTM) potently inhibits ErbB receptor phosphorylation and cell viability of ErbB2-positive breast cancer cells", Investigational New Drugs, Dec. 2014 (available online Aug. 2014), 32(6), pp. 1096-1104.
Herman, S. et al., "Bruton tyrosine kinase represents a promising therapeutic target for treatment of chronic lymphocytic leukemia and is effectively targeted by PCI-32765", Blood, Jun. 2011 (available online Mar. 2011), 117(23), pp. 6287-6296.
Honigberg, L. et al., "The Bruton tyrosine kinase inhibitor PCI-32765 blocks B-cell activation and is efficacious in models of autoimmune disease and B-cell malignancy", PNAS USA, Jul. 2010, 107(29), pp. 13075-13080.
Hung, T. et al., "Wnt5A regulates ABCB1 expression in multidrug-resistant cancer cells through activation of the non-canonical PKA/β-catenin pathway", Oncotarget, Dec. 2014 (available online Oct. 2014), 5(23), pp. 12273-12290.
Junttila, T. et al., "Cleavable ErbB4 isoform in estrogen receptor-regulated growth of breast cancer cells", Cancer Research, Feb. 2005, 65(4), pp. 1384-1393.
Kim, J.-Y. et al., "Prognostic value of ERBB4 expression in patients with triple negative breast cancer", BMC Cancer, Feb. 2016, vol. 16, article 138, doi: 10.1186/s12885-016-2195-3.
Krejci, K. et al., "Receptor Tyrosine Kinases Activate Canonical WNT/β-Catenin Signaling via MAP Kinase/LRP6 Pathway and Direct β-Catenin Phosphorylation", PLOS One, Apr. 2012, 7(4), article e35826, https://doi.org/10.1371/journal.pone.0035826.
Kurppa, K. et al., "Activating ERBB4 mutations in non-small cell lung cancer", Oncogene, Mar. 2016 (available online Jun. 2015), vol. 35, pp. 1283-1291.
Liu, T. et al., "Establishment and characterization of multi-drug resistant, prostate carcinoma-initiating stem-like cells from human prostate cancer cell lines 22RV1", Molecular and Cellular Biochemistry, Jul. 2010 (available online Mar. 2010), 340(1-2), pp. 265-273.
Masso-Valles, D. et al., "Ibrutinib exerts potent antifibrotic and antitumor activities in mouse models of pancreatic adenocarcinoma", Cancer Research, Apr. 2015, 75(8), pp. 1675-1681.
Mendoza-Naranjo, A. et al., "ERBB4 confers metastatic capacity in Ewing sarcoma", EMBO Molecular Medicine, Jul. 2013 (available online May 2013), 5(7), pp. 1019-1034.
Miersch, S. et al., "Nucleic Acid programmable protein arrays: versatile tools for array-based functional protein studies", Current Protocols in Protein Science, Apr. 2011, Chapter 27, Unit 27.2, Supplement 64, pp. 27.2.1-27.2.26.

Hakata, A. et al., "Elevated β-catenin pathway as a novel target for patients with resistance to EGF receptor targeting drugs", Scientific Reports, Aug. 2015, vol. 5, article 13076, doi:10.1038/srep13076.
Niehrs, C., "The complex world of WNT receptor signalling", Nature Reviews Molecular Cell Biology, Dec. 2012 (available online Nov. 2012), 13(12), pp. 767-779.
Pan, Z. et al., "Discovery of selective irreversible inhibitors for Bruton's tyrosine kinase", Chem Med Chem, Jan. 2007 (available online Dec. 2006), 2(1), pp. 58-61.
Patent Cooperation Treaty, International Bureau, International Preliminary Report on Patentability for PCT/US2016/020422, 5 pages, dated Sep. 5, 2017.
Patent Cooperation Treaty, International Searching Authority, International Search Report for PCT/US2016/020422, 2 pages, dated May 31, 2016.
Patent Cooperation Treaty, International Searching Authority, Written Opinion for PCT/US2016/020422, 4 pages, dated May 31, 2016.
Prickett, T. et al., "Analysis of the tyrosine kinome in melanoma reveals recurrent mutations in ERBB4", Nature Genetics, Oct. 2009 (available online Aug. 2009), 41(10), pp. 1127-1132.
Qiu, C. et al., "Mechanism of activation and inhibition of the HER4/ErbB4 kinase", Structure, Mar. 2008, 16(3), pp. 160-467.
Ramachandran, N. et al., "Next generation high density self assembling functional protein arrays", Jun. 2008 (available online May 2008), 5(6), pp. 535-538.
Rauf, F. et al., "Ibrutinib inhibition of ERBB4 reduces cell growth in a WNT5A-dependent manner", Oncogene, available online Feb. 2018, doi:10.1038/s41388-017-0079-x.
Rushworth, S. et al., "BTK inhibitor ibrutinib is cytotoxic to myeloma and potently enhances bortezomib and lenalidomide activities through NF-κb", Cellular Signalling, Jan. 2013 (available online Sep. 2012), 25(1), pp. 106-112.
Sagiv-Barfi, I. et al., "Therapeutic antitumor immunity by checkpoint blockade is enhanced by ibrutinib, an inhibitor of both BTK and ITK", PNAS USA, Mar. 2015 (available online Feb. 2015), 112(9), pp. E966-E972.
Smith, M., "Ibrutinib in B lymphoid malignancies", Expert Opinion on Pharmacotherapy, Jul. 2015, 16(12), pp. 1879-1887.
Volpe, A. et al., "Chromophobe renal cell carcinoma (RCC): oncological outcomes and prognostic factors in a large multicentre series", BJU International, Jul. 2012 (available online Nov. 2011), 110(1), pp. 76-83.
Wang, X .et al., "Bruton's Tyrosine Kinase Inhibitors Prevent Therapeutic Escape in Breast Cancer Cells", Molecular Cancer Therapeutics, Sep. 2016 (available online Jun. 2016), 15(9), pp. 2198-2208.
Williams, C. et al., "ERBB4 is over-expressed in human colon cancer and enhances cellular transformation", Carcinogenesis, Jul. 2015 (available online Apr. 2015), 36(7), pp. 710-718.
Woyach, J. et al., "The B-cell receptor signaling pathway as a therapeutic target in CLL", Blood, Aug. 2012 (available oriline Jun. 2012), 120(6), pp. 1175-1184.
Wu, H. et al., "Discovery of a Potent, Covalent BTK Inhibitor for B-Cell Lymphoma", ACS Chemical Biology, May 2014 (available online Feb. 2014), 9(5), pp. 1086-1091.
Zhang, J. et al., "A phase I study of AST1306, a novel irreversible EGFR and HER2 kinase inhibitor, in patients with advanced solid tumors", Journal of Hematology & Oncology, Mar. 2014, vol. 7, article 22, https://doi.org/10.1186/1756-8722-7-22.

* cited by examiner

Relevant Art

ERBB4 INHIBITORS AND METHODS OF USE THEREOF

CROSS-REFERENCE TO RELATED APPLICATIONS

This application represents the national stage entry of PCT International Application No. PCT/US2016/020422, filed on Mar. 2, 2016 and claims the benefit of U.S. Provisional Patent Application No. 62/128,239, filed Mar. 4, 2015. The disclosure of each of the above-identified applications is incorporated herein by reference as if set forth in its entirety.

STATEMENT REGARDING FEDERALLY SPONSORED RESEARCH OR DEVELOPMENT

Not Applicable.

BACKGROUND

Tyrosine kinases are a family of proteins that catalyze phosphorylation of tyrosine residues in target proteins and play important roles in cellular signaling. Within this large family of proteins is the epidermal growth factor receptor (EGFR) family, which includes the receptor kinases ERBB1 (EGFR1, HER1), ERBB2 (c-Neu, HER2), ERBB3 (HER3), and ERBB4 (HER4). The ERBB kinases regulate a wide range of cellular responses, including cell proliferation, survival, migration and differentiation.

ERBB4 is a receptor tyrosine kinase member of approximately 180 kD. The interaction with its ligand promotes receptor dimerization and autophosphorylation, which leads to the regulation of several key pathways associated with cell proliferation, death and differentiation. Changes in ERBB4 activity through mutations and overexpression are associated with several types of cancers, psychiatric and cardiovascular disorders.

Currently, there are no drugs available for treating diseases that present through over activation of the ERBB4 pathway, such as breast cancer and lung cancer. Further, there are no methods of identifying patients which will be successfully treated with ERBB4 inhibitors, thereby preventing the treatment of patients exhibiting tumors inherently resistant to specific ERBB4 inhibitors.

There remains a great need for drugs that target diseases associated with over activation of the ERBB4 pathway, such as breast cancer and lung cancer, as well as methods of identifying patients likely to be successfully treated with ERBB4 inhibitors.

BRIEF SUMMARY OF THE INVENTION

The present invention provides a method of treating diseases that exhibit an over-activation of the ERBB4 pathway, the method comprising administering to a subject having a disease that exhibits over-activation of the ERBB4 pathway a therapeutically effective amount of an ERBB4 inhibitor such as ibrutinib, wherein the disease is effectively treated. Diseases that exhibit an over-activation of the ERBB4 pathway present a gene expression profile consistent with an ERBB4 sensitive disease and include, for example, breast cancer, lung cancer, endometrial cancer, melanoma, colon cancer, gastric cancer, prostate cancer, ovarian cancer, glioma, and astrocytoma.

In one aspect, the invention provides a Nucleic Acid Programmable Protein Array (NAPPA) suitable for use with protein-tyrosine kinases.

In another aspect, provided herein is a method of treating a disease associated with over-activation of ERBB4 signal transduction, the method comprising administering a therapeutically effective amount of an agent that suppresses ERBB4-mediated signal transduction to a subject having or suspected of having the disease, whereby the disease is treated. The agent that suppresses ERBB4-mediated signal transduction can be an ERBB4 inhibitor selected from the group consisting of a shRNA, a siRNA, a micro-RNA mimic, an antisense oligonucleotide, a small molecule inhibitor of ERBB4, or a protein inhibitor. The ERBB4 inhibitor can be ibrutinib. The ERBB4 inhibitor can be AST1306. The disease associated with over-activation of ERBB4 signal transduction can be selected from the group consisting of breast cancer, lung cancer, endometrial cancer, melanoma, colon cancer, gastric cancer, prostate cancer, ovarian cancer, glioma, and astrocytoma. The disease can present a gene expression profile consistent with an ERBB4 sensitive disease.

In a further aspect, provided herein is a pharmaceutical composition for treating disease associated with over-activation of ERBB4 signal transduction, comprising: (1) an agent that suppresses ERBB4-mediated signal transduction; and (2) a pharmaceutically acceptable carrier, wherein the agent reduces the level of ERBB4 gene expression or a biological activity of the ERBB4 protein. The agent can be ibrutinib. The agent can be AST1306. The disease associated with over-activation of ERBB4 signal transduction can be selected from the group consisting of breast cancer, lung cancer, endometrial cancer, melanoma, colon cancer, gastric cancer, prostate cancer, ovarian cancer, glioma, and astrocytoma.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof.

DETAILED DESCRIPTION

Figure 1:
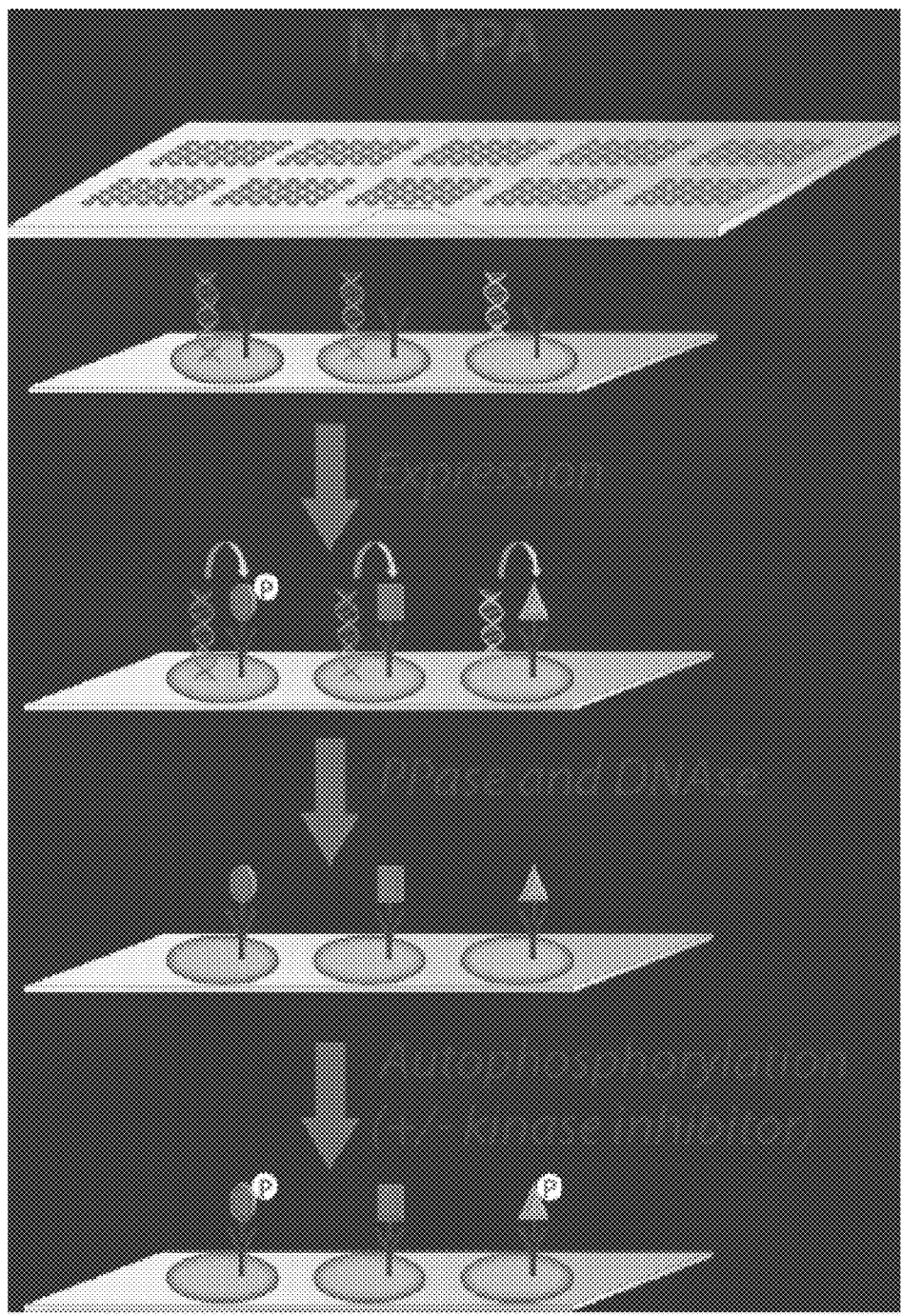
FIG. 1. Schematic representation of Nucleic Acid Programmable Protein Array (NAPPA) methodology for the study of kinase inhibitors.

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

In the specification and in the claims, the terms "including" and "comprising" are open- ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green et al., Eds. (1999), *Genome Analysis: A Laboratory Manual Series* (Vols. I-IV); Weiner, Gabriel, Stephens, Eds. (2007), *Genetic Variation: A Laboratory Manual;* Dieffenbach, Dveksler, Eds. (2003), *PCR Primer: A Laboratory Manual;* Bowtell and Sambrook (2003), *DNA Microarrays: A Molecular Cloning Manual;* Mount (2004), *Bioinformatics: Sequence and Genome Analysis;* Sambrook and Russell (2006), *Condensed Protocols from Molecular Cloning: A Laboratory Manual;* and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, *"Oligonucleotide Synthesis: A Practical Approach"* 1984, IRL Press, London; Nelson and Cox (2000), *Lehninger, Principles of Biochemistry* $3^{rd}$ Ed., W. H. Freeman Pub., New York, N.Y.; and Berg et al. (2002) *Biochemistry,* $5^{th}$ Ed., W. H. Freeman Pub., New York, N.Y., all of which are herein incorporated in their entirety by reference for all purposes.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

In one embodiment, the invention provides a method of treating diseases that present over-activation of the ERBB4 (V-Erb-B2 Avian Erythroblastic Leukemia Viral Oncogene Homolog 4) pathway, including, but not limited to breast, lung, melanoma, colon, gastric, prostate, ovarian, and glioma. The method comprises administering to a subject having a disease that exhibits over-activation of the ERBB4 pathway and a gene expression profile consistent with an ERBB4-sensitive profile a therapeutically effective amount of an ERBB4 inhibitor, wherein the disease is effectively treated.

In one aspect, provided herein are methods of treating a disease, condition, or disorder associated with over-activation of the ERBB4 pathway in a subject. For example, the present invention provides methods comprising administering to a subject in need thereof an inhibitor of ERBB4, whereby the disease, condition, or disorder is treated. As used herein, the terms "treating," "treat," and "treatment" refer to the management and care of a patient for the purpose of combating the disease, condition, or disorder. The terms embrace both preventative, i.e., prophylactic, and palliative treatments. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. As used herein, the terms "preventing" and "prevent" refer not only to a complete prevention of a certain disease or condition, but also to partially or substantially attenuating, reducing the risk of, or delaying the development or recurrence of the disease or condition to which the term applies.

As used herein, the term "subject" refers to an individual having, suspected of having, or susceptible to having a disease or condition associated with over-activation of the ERBB4 pathway. By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, the term "ERBB4 inhibitor" refers to any agent that is capable of reducing the level of ERBB4 gene expression or a biological activity of the ERBB4 protein. The term "gene expression" as used herein refers to the process of transcription of mRNA from a coding sequence, translation of mRNA into a polypeptide, and post-translational modifications such as phosphorylation and glycosylation. A person of ordinary skill in the art would understand that an ERBB4 may also have anti-ERBB4 pathway activity. Examples of ERBB4 inhibitors include, without limitation, small molecules that target ERBB4, RNA interference agents, antisense RNA, and anti-ERBB4 antibodies. These ERBB4 inhibitors also include those attached to, complexed with, inserted into, or otherwise associated with the agents that target the ERBB4 inhibitors to particular cell types or alter the metabolic properties, pharmacokinetic characteristics, or other characteristics of the ERBB4 inhibitors. As used herein, the term "RNA interference agent" refers to small nucleic acid molecules used for RNA interference (RNAi), such as short interfering RNA (siRNA), double-stranded RNA (dsRNA), microRNA (miRNA) and short hairpin RNA (shRNA) molecules. The term "antisense RNA," as used herein, refers to a nucleotide sequence that comprises a sequence substantially complementary to the whole or a part of an mRNA molecule and is capable of binding to the mRNA.

As used herein, the term "therapeutically effective amount" refers to an amount effective, at dosages and for periods of time necessary, to achieve the desired therapeutic result, e.g., sufficient to inhibit gene expression or protein activity of ERBB4 to a desired level. The effective amount of an ERBB4 inhibitor may vary according to factors such as the disease state, age, and weight of the subject, and the ability of the particular agent or agents to elicit a desired response in the subject. Dosage regimens may be adjusted to provide the optimum therapeutic response. An effective amount is also one in which any toxic or detrimental effects (e.g., side effects) of the agent(s) are outweighed by the therapeutically beneficial effects. Toxicity and therapeutic efficacy of such agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents which exhibit large therapeutic indices are preferred. While agents that exhibit toxic side effects may be used, care should be taken to design a delivery system that targets such compounds to the site of affected tissue in order to minimize potential damage to uninfected cells and, thereby, reduce side effects.

In some cases, an ERBB4 inhibitor is a small molecular weight agent capable of interfering with ERBB4-mediated signaling transduction. In one embodiment, the ERBB4 inhibitor is a compound according to the structure:

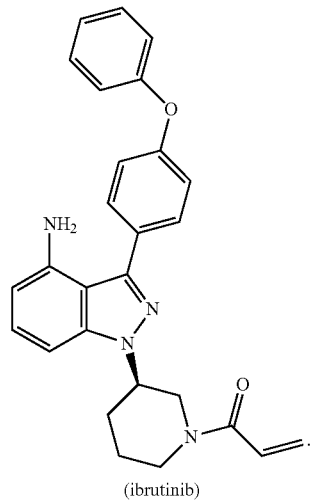 [SMILES: C=CC(=O)N1CCC[C@@H](n2nc(-c3ccc(Oc4ccccc4)cc3)c3c(N)cccc32)C1]

(ibrutinib)

Ibrutinib

Ibrutinib, also known as PCI-32765 and marketed under the name Imbruvica, is an anticancer drug targeting B-cell malignancies including chronic lymphocytic leukemia (CLL), small lymphocytic lymphoma (SLL), mantle cell lymphoma (MCL), diffuse large B-cell lymphoma (DLBCL) and multiple myeloma (cancer of plasma cells, a type of white blood cell present in bone marrow). At present, ibrutinib is administered orally in clinical trials, through the gastrointestinal tract, at high clinical doses (420 mg/day or 840 mg/day) to patients with CLL and SLL to obtain the desired therapeutic effect. It was approved by the US FDA in November 2013 for the treatment of mantle cell lymphoma and in February 2014 for the treatment of chronic lymphocytic leukemia. It is an orally-administered, selective and covalent inhibitor of the enzyme Bruton's tyrosine kinase (BTK). Ibrutinib was disclosed in U.S. Pat. No. 7,514,444, issued on Apr. 7, 2009.

BTK is a member of the Tec tyrosine kinase family. BTK is expressed in most hematopoietic cells such as B cells, mast cells, and macrophages, but not in T cells, natural killer cells, and plasma cells. BTK plays a role in the development and activation of B cells. Mutations in the human BTK gene cause the inherited disease X-linked agammaglobulinemia (XLA), with lack of peripheral B cells and low levels of serum Ig. In XLA, the primary immune deficit is B cell specific. The development of drugs which inhibit BTK can have therapeutic significance in the treatment of both B cell-related hematological cancers (e.g., non-Hodgkin lymphoma (NHL) and B cell chronic lymphocytic leukemia (B-CLL), and autoimmune diseases (e.g., rheumatoid arthritis, Sjogrens syndrome, IBD, lupus, and asthma).

We used protein microarrays to screen hundreds of protein kinases against ibrutinib and identified ERBB4/Her4 (V-Erb-B2 Avian Erythroblastic Leukemia Viral Oncogene Homolog 4) as a new target. Protein microarrays were generated using NAPPA (Nucleic acid programmable protein array) methodology, which permits the use of freshly expressed proteins for functional assays (FIG. 1). In NAPPA, cDNAs coding for the target of interest are cloned into an expression vector, which generates a fusion (Halo Tag, GST, etc.) to the target, and spotted onto a glass slide.

Then to each spot, a HeLa cell in vitro transcription-translation reagent is added, whereby the fusion gene is transcribed into mRNA and translated. The nascent proteins are captured to the slide with antibody to the fusion partner (i.e., HaloTag-ligand, α-GST antibody) that is spotted adjacent to the DNA during the manufacture of the array. This method allows for up to thousands of protein targets to be arrayed. NAPPA microarrays can be expressed using an in vitro transcription and translation system (IVTT), and the anti-tag antibody captures newly synthesized proteins. Following expression, the microarrays were treated with phosphatase to remove any phosphorylation that occurred during the expression of the proteins.

In another aspect, therefore, provided herein are targets that have been generated by NAPPA for use in screens.

Figures 2A, 2B, 2C, 2D:
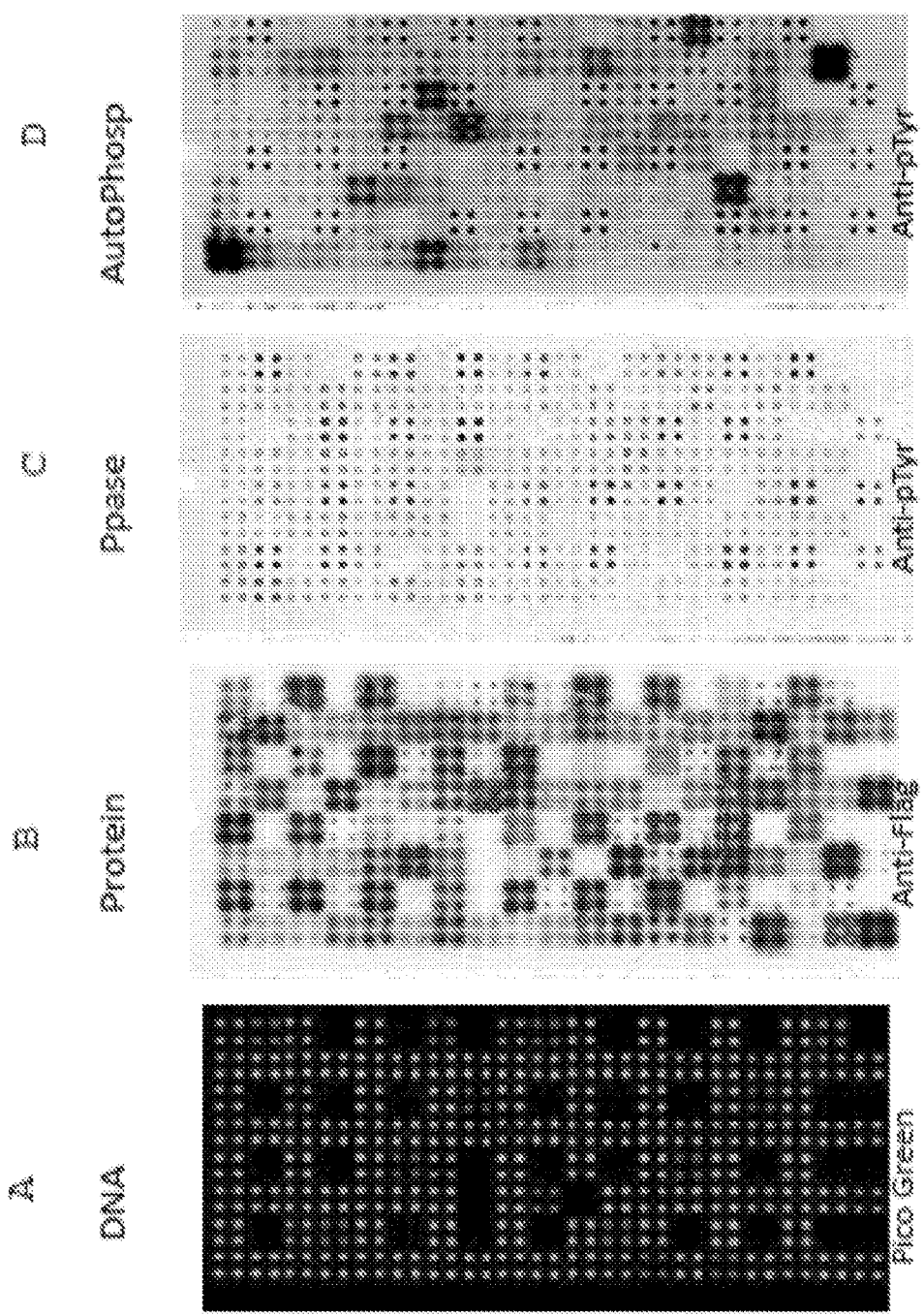
FIG. 2A. Typical signal observed on NAPPA arrays in distinct steps of the kinase assay. DNA levels measured by Picogreen.
FIG. 2B. Protein display measured with anti-flag antibody after protein expression.
FIG. 2C. Phosphorylation levels measured by anti-p-tyr antibody after phosphatase treatment.
FIG. 2D. Phosphorylation levels measured by anti-p-tyr antibody after autophosphorylation reaction.

De-phosphorylated arrays were then incubated with kinase buffer containing various concentrations of ATP and/or kinase inhibitors. The kinase activity was measured as end point assay using anti-phopho tyrosine antibody linked to cy3 as the detecting agent (FIG. 2). The data was normalized using positive control features present in each array. The signal obtained in the microarray treated with kinase inhibitor was interpolated in the curve obtained from arrays treated with buffer only (lower phosphorylation level—0%) or treated with ATP and DMSO (maximum phosphorylation level—100%). Among the 105 protein kinases tested, a handful of targets were identified for ibrutinib including BTK (canonical target), ERBB4, and Tec (Table 1).

TABLE 1

Kinase activity registered on NAPPA arrays exposed to various concentrations of Ibrutinib.

| name | kinase activity (%) | | |
|---|---|---|---|
| | DMSO | 0.1 uM Ibrutinib | 1 uM Ibrutinib |
| BTK | 100 | 38.3 | 5.5 |
| ERBB4/HER4 | 100 | 67.1 | 44.1 |
| Tec | 100 | 68.7 | 62.0 |
| EGFR/ERBB1 | 100 | 81.2 | 89.7 |
| FGFR4 | 100 | 81.5 | 99.1 |
| TESK2 | 100 | 85.8 | 83.5 |
| EPHA1 | 100 | 87.2 | 99.1 |
| EPHA3 | 100 | 89.1 | 101.3 |
| SYK | 100 | 90.5 | 109.7 |
| BCRABL | 100 | 92.0 | 93.1 |
| EPHA7 | 100 | 92.3 | 94.9 |
| DYRK2 | 100 | 97.3 | 82.3 |
| FGFR1 | 100 | 98.8 | 105.8 |
| YES1 | 100 | 99.3 | 90.9 |
| TNK2 | 100 | 99.9 | 86.9 |
| ERBB3/HER3 | 100 | 100.0 | 206.1 |
| Abl1 | 100 | 101.5 | 104.3 |
| Yes1 | 100 | 101.6 | 97.6 |
| HCK | 100 | 102.1 | 105.0 |

Figure 3A:
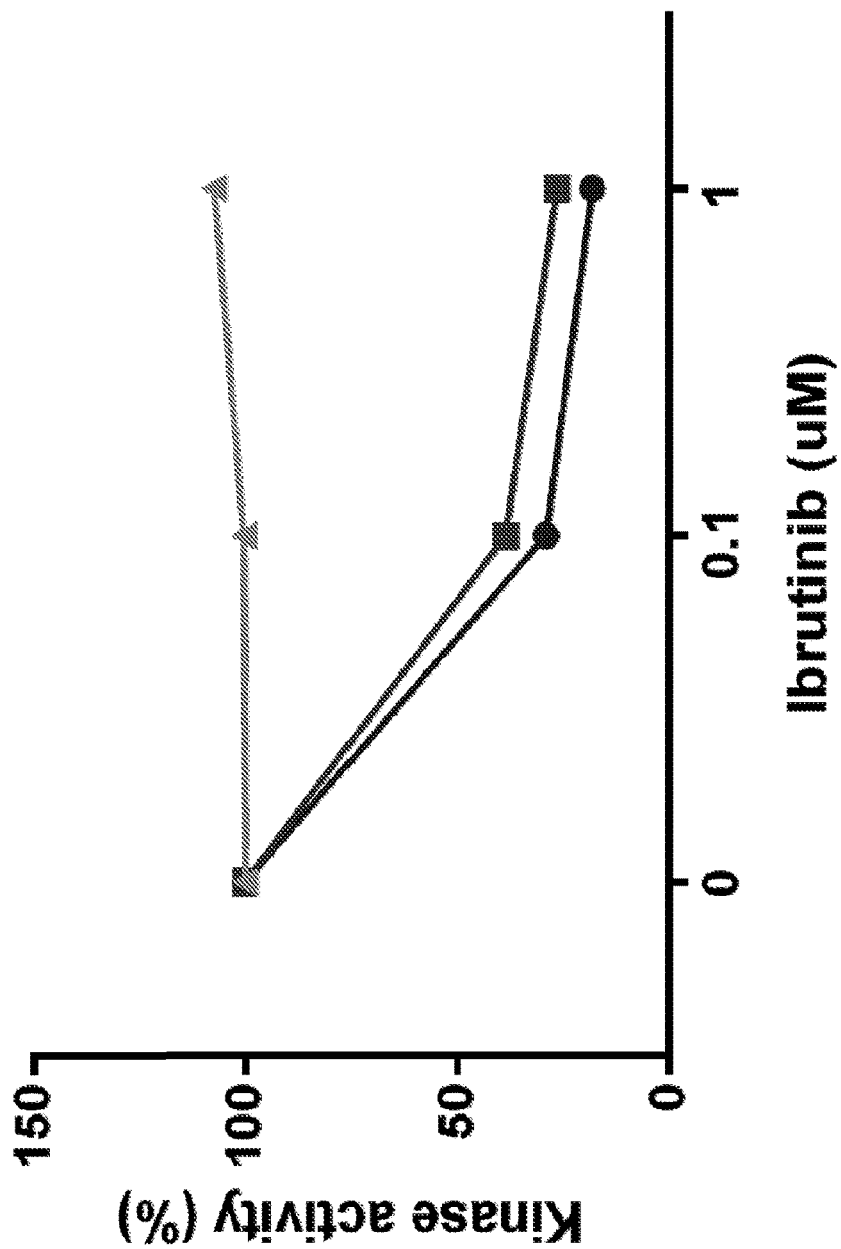
FIG. 3A. Erbb4 and BTK are inhibited by Ibrutinib at comparable levels -radioactive kinase assay.

The microarray data was validated in vitro using gold-standard methodologies. First, radioactive kinase assays were performed with purified protein kinases incubated with radioactive ATP and increasing concentrations of kinase inhibitors. The kinase activity was measured through the levels of radioactive phosphorylation present in each kinase. Our data shows that BTK and ERBB4 had more than 80% of their activity inhibited by 1 uM of Ibrutinib, while Abl1 (negative control) was 100% active at the same drug concentration (FIG. 3A).

Figure 3B:
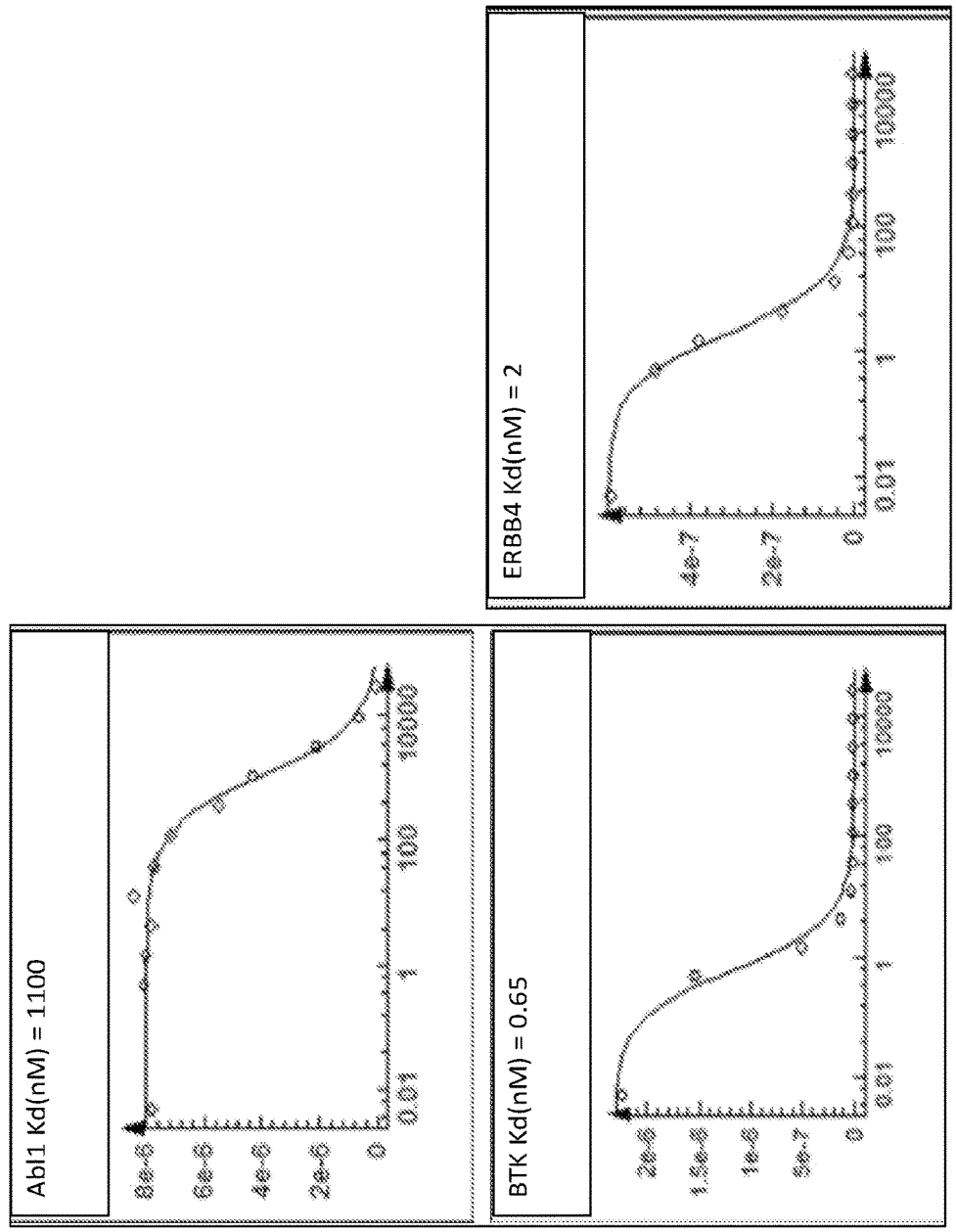
FIG. 3B. Erbb4 and BTK are inhibited by Ibrutinib at comparable levels-active-site dependent competition binding assay.

Second, active-site dependent competition binding assay was performed; soluble protein kinases tagged with a DNA tag were incubated with an affinity column in the presence of increasing concentration of kinase inhibitor. The amount of kinase bound to the column is proportional to the kinase activity and it was measured by Q-PCR. The final results were expressed as biding affinity (Kd) between kinase and Ibrutinib, with 0.64 nM for BTK, 2 nM for ERBB4 and 1100 nM for Abl1 (FIG. 3B). These results show that ibrutinib can inhibit ERBB4 in vivo and that this inhibition can be achieved with drug concentrations used routinely in patients.

The inhibition of ERBB4 by ibrutinib was tested in vivo using cell lines that overexpressed ERBB4 and did not express BTK, assuring that any response observed was due to the expression of the new target (ERBB4) and not the canonical target (BTK). Cell lines were treated for 7 days with 1 uM ibrutinib and the number of viable cells was measured by Trypan blue exclusion test. The growth inhibition was calculated for each cell line as a percentage of the growth achieved in the presence of Ibrutinib compared to the control DMSO. The following inhibition rates were observed: H716 (75%), KLE (73%), H661 (72%), H522 (60%), OVKATE (45%), OVSAHO (37%), HEC59 (31%), COV434 (15%), 1321N1 (10%), COV318 (8%) and H146 (0%).

Figure 4:
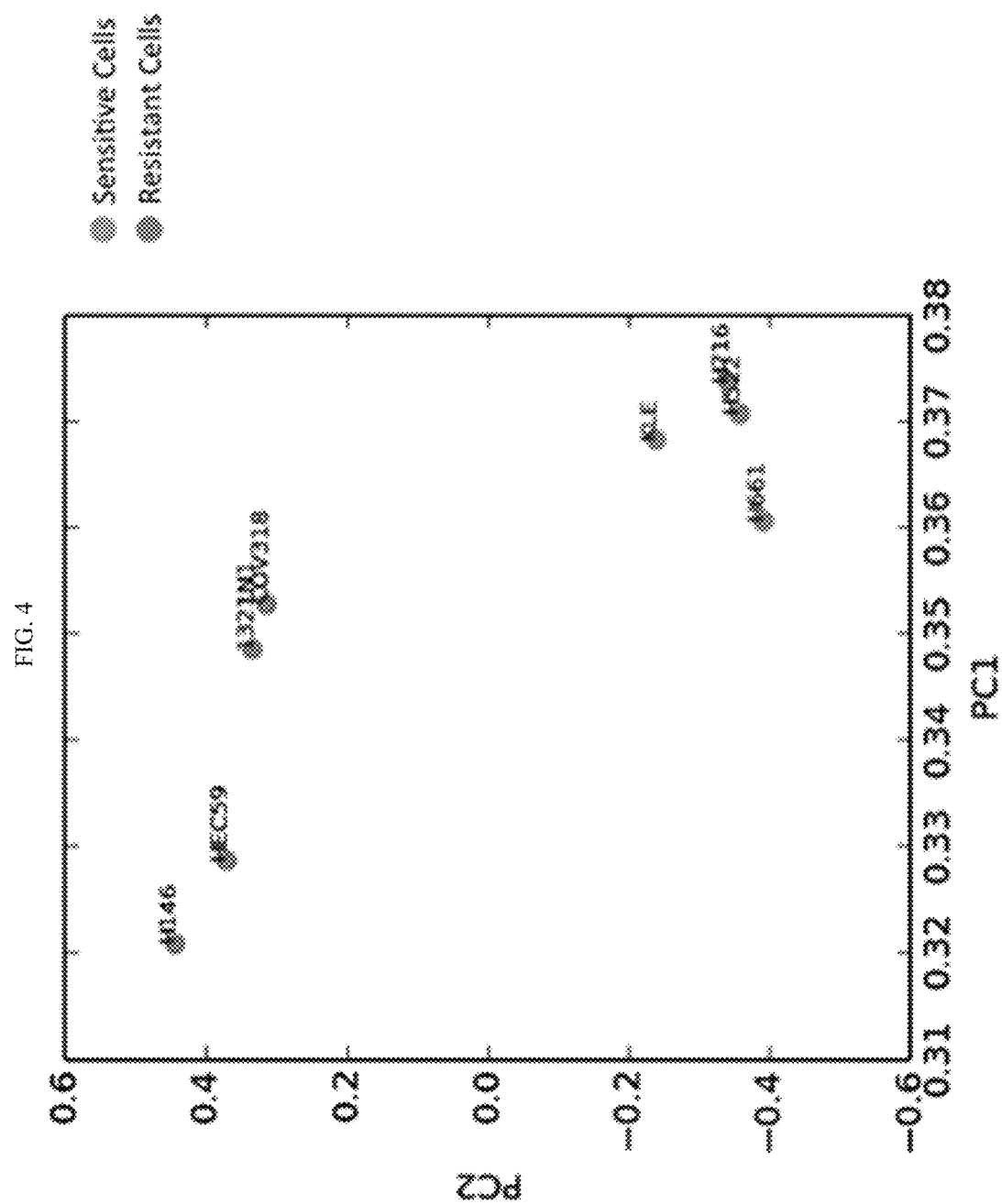
FIG. 4. Classification of ibrutinib-resistant and -sensitive cells by gene expression values of 401 differentially expressed genes by principal component analysis.

To identify gene expression profiles (or signatures) that are associated with ibrutinib sensitivity, mRNA expression levels in ibrutinib-sensitive (H716, KLE, H661, and H522) and ibrutinib-resistant (1321N1, Hec59, COV318, and H416) cell lines were measured by next-generation sequencing, also known as RNA-seq. Briefly, the mRNA samples from basal (i.e. not treated with ibrutinib) state cells were converted to cDNA libraries, which were paired-end (2×100 bp) sequenced by Illumina HiSeq-2000 sequencer. The sequence reads were aligned to the Ensembl human genome by the bowtie2 software, and the aligned read counts were quantified and normalized against gene sizes and the number of reads by the cufflinks software. To identify differentially expressed gene between ibrutinib-resistant and -sensitive cells, we performed a non-parametric test (Mann-Whitney U test) and selected the initial pool of 401 genes with P values <0.05. These genes effectively classified ibrutinib-sensitive and -resistant cells into two separate groups (FIG. 4), and thus can potentially predict the responsiveness to ibrutinib in ERBB4-positive/BTK-negative cancers.

To identify biological processes that may govern the ibrutinib responsiveness, pathway analysis was performed on the 401 differentially expressed genes, based on information in public pathway databases (Reactome, Panther, and NCI Pathway Interaction Database). Since ERBB4 is a receptor tyrosine kinase that regulates downstream signaling events, we searched specifically any signaling pathways of which gene expression profiles were significantly different between ibrutinib-resistant and -sensitive cells by the Pathifier software. After removing redundant pathway terms, 29 signaling pathways were found significantly deregulated (Table 2), which included interferon, G protein-coupled receptors, cytokine receptors, growth factor receptors (including ERBB4), and WNT signaling pathways.

TABLE 2

Deregulated signaling pathways between ibrutinib-resistant and -sensitive cells.

| Pathway | P_value |
|---|---|
| RIG-I/MDA5 mediated induction of IFN-alpha/beta pathways (R) | 0.010 |
| Glucocorticoid receptor regulatory network (N) | 0.011 |
| PDGF signaling pathway (P) | 0.015 |

TABLE 2-continued

Deregulated signaling pathways between ibrutinib-resistant and -sensitive cells.

| Pathway | P_value |
|---|---|
| Interleukin signaling pathway (P) | 0.015 |
| Validated targets of C-MYC transcriptional repression (N) | 0.023 |
| Direct p53 effectors (N) | 0.026 |
| Focal Adhesion (W) | 0.029 |
| Signaling by Insulin receptor (R) | 0.029 |
| Signaling by FGFR (R) | 0.032 |
| Signaling events mediated by VEGFR1 and VEGFR2 (N) | 0.033 |
| PI3K/AKT activation (R) | 0.033 |
| Cadherin signaling pathway (P) | 0.036 |
| Signaling by Wnt (R) | 0.040 |
| Signaling by EGFR in Cancer (R) | 0.040 |
| PI3K events in ERBB2 signaling (R) | 0.040 |
| PI3K events in ERBB4 signaling (R) | 0.041 |
| Regulation of cholesterol biosynthesis by SREBP (SREBF) (R) | 0.042 |
| PLK1 signaling events (N) | 0.042 |
| Leptin signaling pathway (W) | 0.046 |
| Toll-Like Receptors Cascades (R) | 0.046 |
| Signaling by NGF (R) | 0.047 |
| EPO signaling pathway (N) | 0.047 |
| Kit receptor signaling pathway (W) | 0.047 |

Since these pathways were identified from cell lines of different cancer types (lung, endometrial, colon, ovarian, and astrocytoma), they represent common biological functions that contribute ibrutinib-resistance, regardless of tissue origins. Therefore, these pathway-based molecular signatures are likely applicable to a broad spectrum of patients with ERBB4-positive and BTK-negative expression patterns.

In parallel, individual differentially expressed genes were manually annotated for their known functions based on evidence in literatures. Notably, among the top 30 genes with the smallest P values (by Mann-Whitney U test), 5 genes were associated with the WNT pathway (Table 3).

TABLE 3

Top raked differentially expressed genes between ibrutinib-resistant and -sensitive cells.

| Gene ID | Symbol | Description | Log2 (Sen/Res) | MW_p |
|---|---|---|---|---|
| 22943 | DKK1* | dickkopf WNT signaling pathway inhibitor 1 | 6.1 | 0.021 |
| 2719 | GPC3* | glypican 3 | 5.8 | 0.021 |
| 51386 | EIF3L | eukaryotic translation initiation factor 3, subunit L | 1.4 | 0.021 |
| 653489 | RGPD3 | RANBP2-like and GRIP domain containing 3 | 1.2 | 0.021 |
| 6578 | SLCO2A1 | solute carrier organic anion transporter family, member 2A1 | 0.8 | 0.021 |
| 8987 | STBD1 | starch binding domain 1 | 0.7 | 0.021 |
| 56125 | PCDHB11 | protocadherin beta 11 | -2.1 | 0.021 |
| 493911 | PHOSPHO2 | phosphatase, orphan 2 | -1.1 | 0.021 |
| 645843 | TMEM14E | transmembrane protein 14E | -0.8 | 0.021 |
| 7593 | MZF1 | myeloid zinc finger 1 | -0.7 | 0.021 |
| 10060 | ABCC9 | ATP-binding cassette, sub-family C (CFTR/MRP), member 9 | -0.7 | 0.021 |
| 30061 | SLC40A1* | solute carrier family 40 (iron-regulated transporter), member 1 | 2.6 | 0.027 |
| 283120 | H19 | H19, imprinted maternally expressed transcript (non-protein coding) | 2.2 | 0.027 |
| 576 | BAI2 | brain-specific angiogenesis inhibitor 2 | 2.0 | 0.027 |
| 90075 | ZNF30 | zinc finger protein 30 | 1.4 | 0.027 |
| 55885 | LMO3 | LIM domain only 3 (rhombotin-like 2) | -6.8 | 0.027 |
| 54809 | SAMD9 | sterile alpha motif domain containing 9 | -2.4 | 0.027 |
| 5998 | RGS3* | regulator of G-protein signaling 3 | -2.4 | 0.027 |
| 146434 | ZNF597 | zinc finger protein 597 | -2.3 | 0.027 |
| 7474 | WNT5A* | wingless-type MMTV integration site family, member 5A | -2.0 | 0.027 |
| 56122 | PCDHB14 | protocadherin beta 14 | -1.9 | 0.027 |
| 400221 | FLJ22447 | uncharacterized LOC400221 | -1.3 | 0.027 |
| 51005 | AMDHD2 | amidohydrolase domain containing 2 | -1.3 | 0.027 |
| 79788 | ZNF665 | zinc finger protein 665 | -1.3 | 0.027 |
| 158135 | TTLL11 | tubulin tyrosine ligase-like family, member 11 | -0.8 | 0.027 |
| 284352 | PPP1R37 | protein phosphatase 1, regulatory subunit 37 | -0.8 | 0.027 |
| 8335 | HIST1H2AB | histone cluster 1, H2ab | -0.7 | 0.027 |
| 163486 | DENND1B | DENN/MADD domain containing 1B | 2.9 | 0.029 |
| 55640 | FLVCR2 | feline leukemia virus subgroup C cellular receptor family, member 2 | 2.8 | 0.029 |
| 11043 | MID2 | midline 2 | 2.7 | 0.029 |
| 57156 | TMEM63C | transmembrane protein 63C | 2.1 | 0.029 |
| 23052 | ENDOD1 | endonuclease domain containing 1 | 1.6 | 0.029 |
| 100130691 | LOC100130691 | uncharacterized LOC100130691 | 1.3 | 0.029 |
| 10409 | BASP1 | brain abundant, membrane attached signal protein 1 | -4.4 | 0.029 |
| 4055 | LTBR | lymphotoxin beta receptor (TNFR superfamily, member 3) | -2.9 | 0.029 |
| 7594 | ZNF43 | zinc finger protein 43 | -2.5 | 0.029 |
| 8355 | HIST1H3G | histone cluster 1, H3g | -1.4 | 0.029 |
| 113655 | MFSD3 | major facilitator superfamily domain containing 3 | -1.3 | 0.029 |
| 115950 | ZNF653 | zinc finger protein 653 | -0.9 | 0.029 |
| 7767 | ZNF224 | zinc finger protein 224 | -0.6 | 0.029 |

*WNT-related genes

Figure 5:
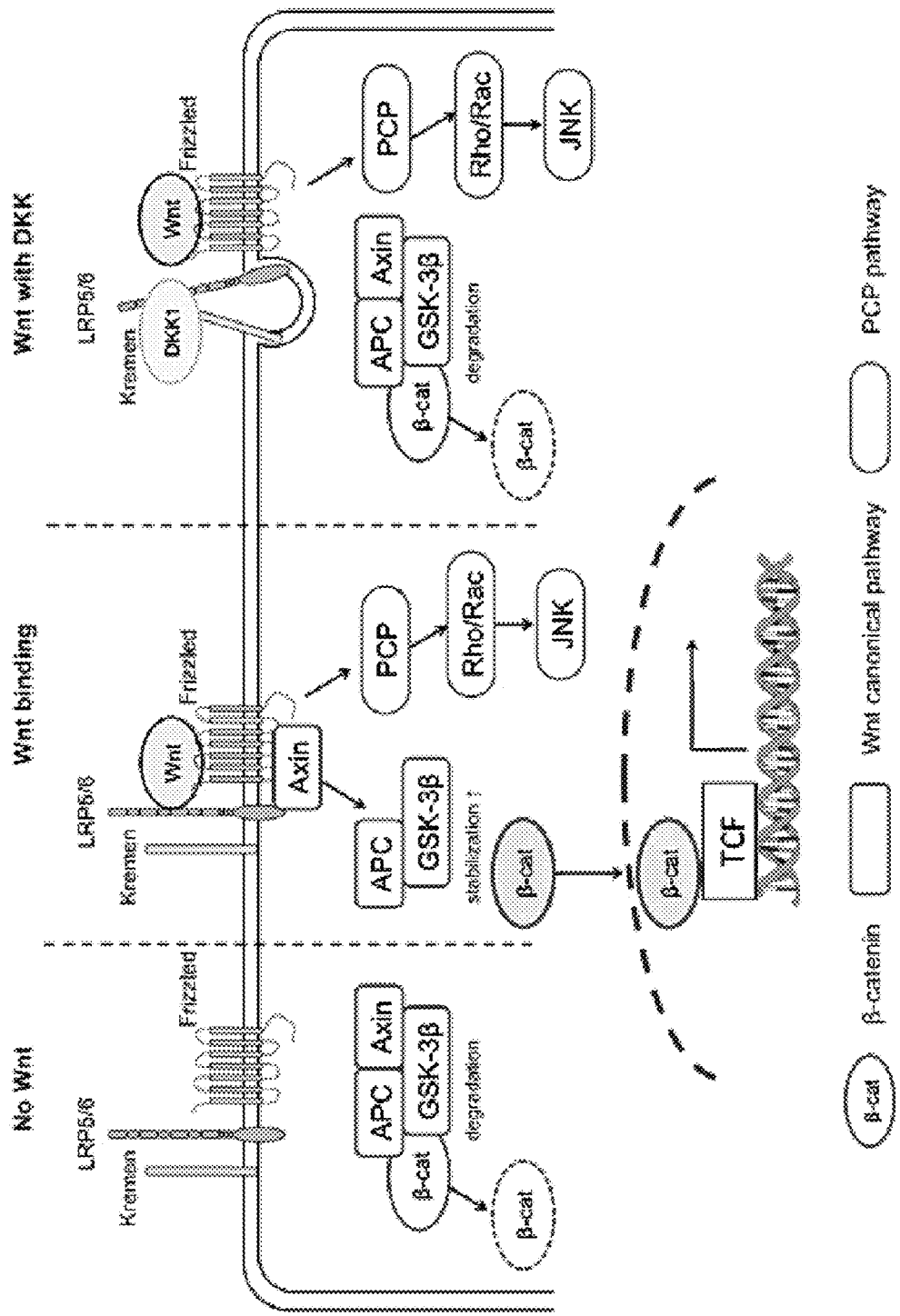
FIG. 5. WNT pathway.
Figure 6:
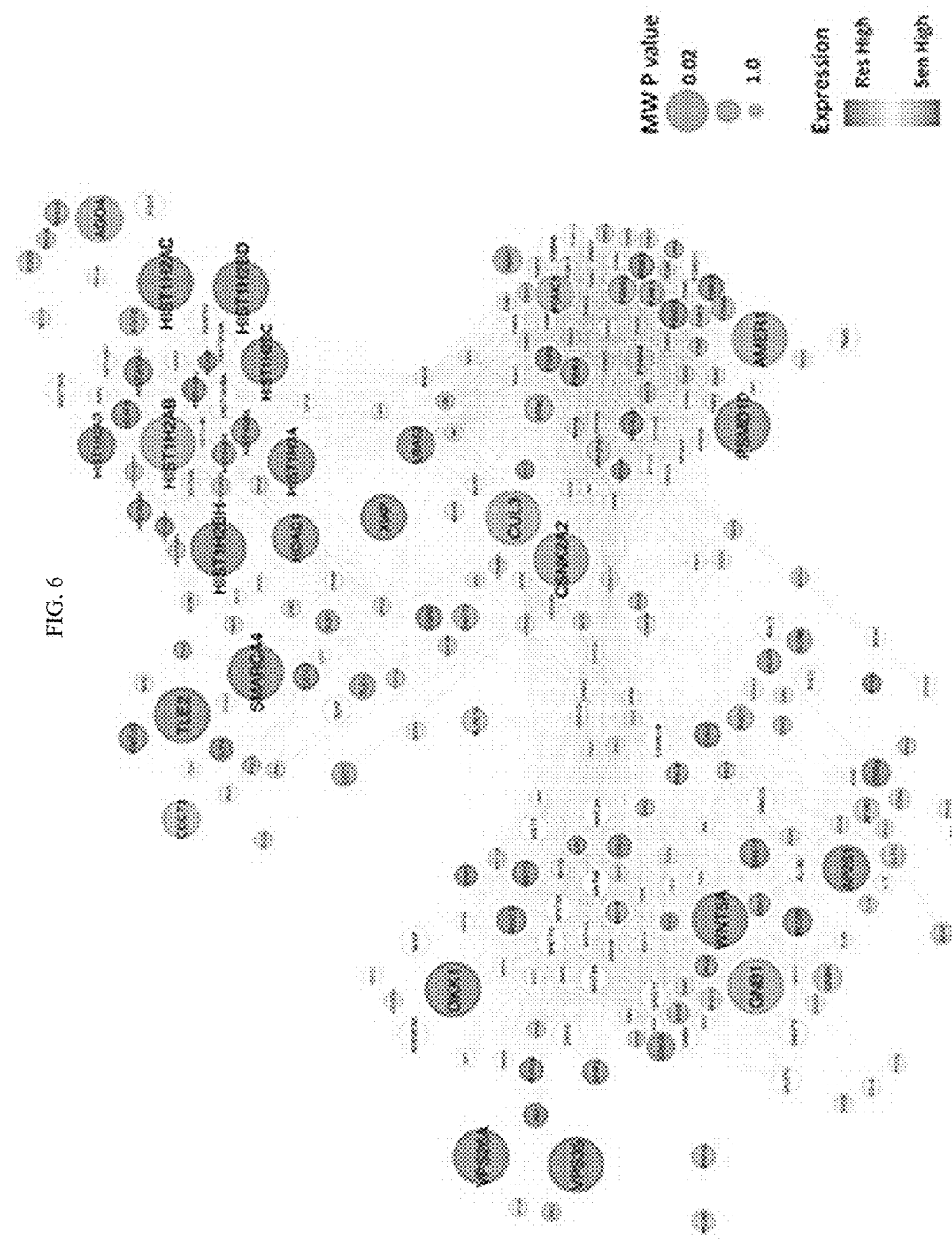
FIG. 6. Differential expression of WNT pathway genes between ibrutinib-resistant and -sensitive cells.

The WNT pathway refers to a group of proteins that regulate signal transduction events originated from the extracellular WNT proteins (FIG. 5), which play important roles in tumor growth and metastasis. Detailed examination on expression of all WNT pathway genes and their functional interactors (based on Reactome database, FIG. 6) revealed that several WNT ligands (WNT5A, WNT3, and WNT7A), WNT regulators (DKK1), signaling molecules (GNB1, GNG11, and CSNK2A2), protein sorting/processing (VPS26A, VPS35, PSMD10, AMER1, and CUL3), and transcriptional regulation (SMARCA4, TLE2, and histones) were differentially expressed. Importantly, as shown in Table 3 and FIG. 6, WNT5A (an activator of WNT pathway) was up-regulated, and DKK1 (an inhibitor of WNT pathway) was down-regulated in ibrutinib-resistant cells, suggesting a synergistic activation of the WNT pathway.

Figure 7:
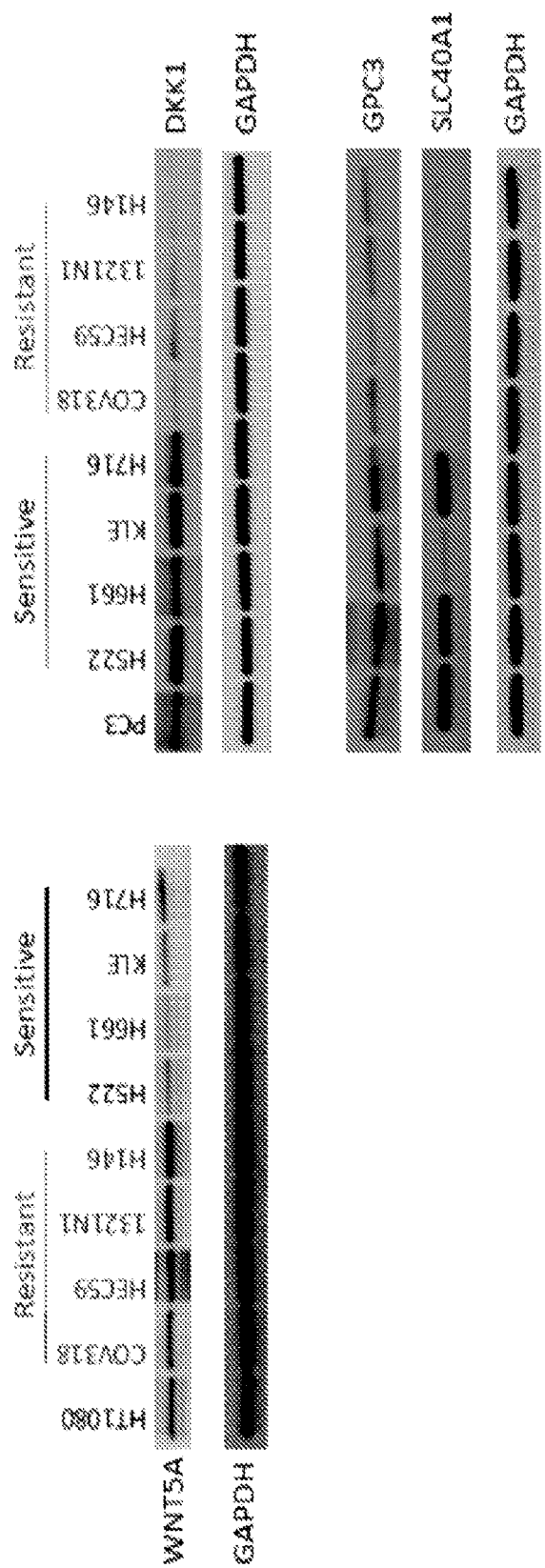
FIG. 7. Protein levels of differentially expressed WNT pathway gene.

Confirming differential expression at the protein level, Western blotting showed that abundances of WNT5A and DKK1 proteins were correlated with their mRNA levels (FIG. 7). In addition, two other differentially expressed WNT pathway genes, GPC3 and SLC40A1, were down-regulated in ibrutinib-sensitive cells (FIG. 7), in agreement with RNA-Seq data (Table 3). Taken together, results from both pathway-level and gene-level analyses suggests that activity of the WNT pathway may determine the sensitivity to ibrutinib in ERBB4-expressing cancer cells. We believe we can use WNT pathway as a predictor. The final set of genes would be less than 10 genes.

In addition to providing biological insights on ERBB4 functions and ibrutinib sensitivity, identification of WNT pathway led us to build a molecular signature for prediction of ibrutinib responsiveness and stratification of cancer patients. Although the entire WNT pathway genes can be utilized, as a proof-of-principal, we first tested if a simple gene expression signature with two genes (DKK1 and WNT5A) could classify ibrutinib-sensitive and -resistant cells. In our RNA-Seq data, all sensitive cell lines showed positive DKK1/WNT5A ratios (i.e., reduced WNT pathway activities), while all resistant cell lines had negative DKK1/WNT5A ratios (i.e., higher WNT pathway activity) (Table 4).

TABLE 4

Association of DKKI/WNT5A ratio with ibrutinib responsiveness in RNA-seq.

| | DKK1 | WNT5A | Log2 (DKK1/WNT5A) | % Survival |
|---|---|---|---|---|
| H661 | 8.0 | 0.0 | 7.98 | 28.2 |
| H716 | 4.1 | 0.0 | 4.09 | 25.5 |
| KLE | 2.4 | 1.3 | 1.09 | 27.2 |
| H522 | 0.6 | 0.0 | 0.57 | 41.0 |
| H146 | 0.0 | 1.6 | −1.63 | 100.0 |
| 1321N1 | 0.0 | 2.3 | −2.32 | 89.7 |
| HEC59 | 0.0 | 2.6 | −2.62 | 68.8 |
| COV318 | 0.0 | 3.0 | −2.96 | 91.5 |

In addition, the ratios were strongly correlated (Pearson's R: −0.798) with the percentage of viable cells after a 24-hour treatment of 1 nM ibrutinib (Table 4). To verify this result, we obtained a publically available gene expression dataset from the CCLE (cancer cell line encyclopedia) database generated by the Broad Institute, which contains Affymetrix microarray-based gene expression profiles of 1,035 cancer cell lines, including the 8 cell lines used in our study. Despite the fundamental difference in expression measurement techniques from RNA-Seq, the DKK1/WNT5A ratio correctly classified all 8 cells into ibrutinib-sensitive and -resistant groups with a strong correlation to the survival ratio (Pearsons's R: 0.897) (Table 5).

TABLE 5

Association of DKKI/WNT5A ratio with ibrutinib responsiveness in CCLE Microarray.

| | DKK1 | WNT5A | Log2 (DKK1/WNT5A) | % Survival |
|---|---|---|---|---|
| H661 | 13.5 | 3.7 | 9.81 | 28.2 |
| H716 | 10.5 | 3.6 | 6.94 | 25.5 |
| KLE | 8.8 | 5.3 | 3.45 | 27.2 |
| H522 | 5.7 | 3.9 | 1.77 | 41.0 |
| HEC59 | 3.9 | 5.2 | −1.32 | 68.8 |
| H146 | 4.6 | 7.1 | −2.51 | 100.0 |
| COV318 | 4.4 | 7.4 | −3.00 | 91.5 |
| 1321N1 | 4.5 | 7.7 | −3.25 | 89.7 |

As discussed above, we identified a large pool of differentially expressed genes in the WNT pathway as wells other signaling pathways, which can be utilized to build further refined molecular signatures of predicting ibrutinib responsiveness.

Figure 8:
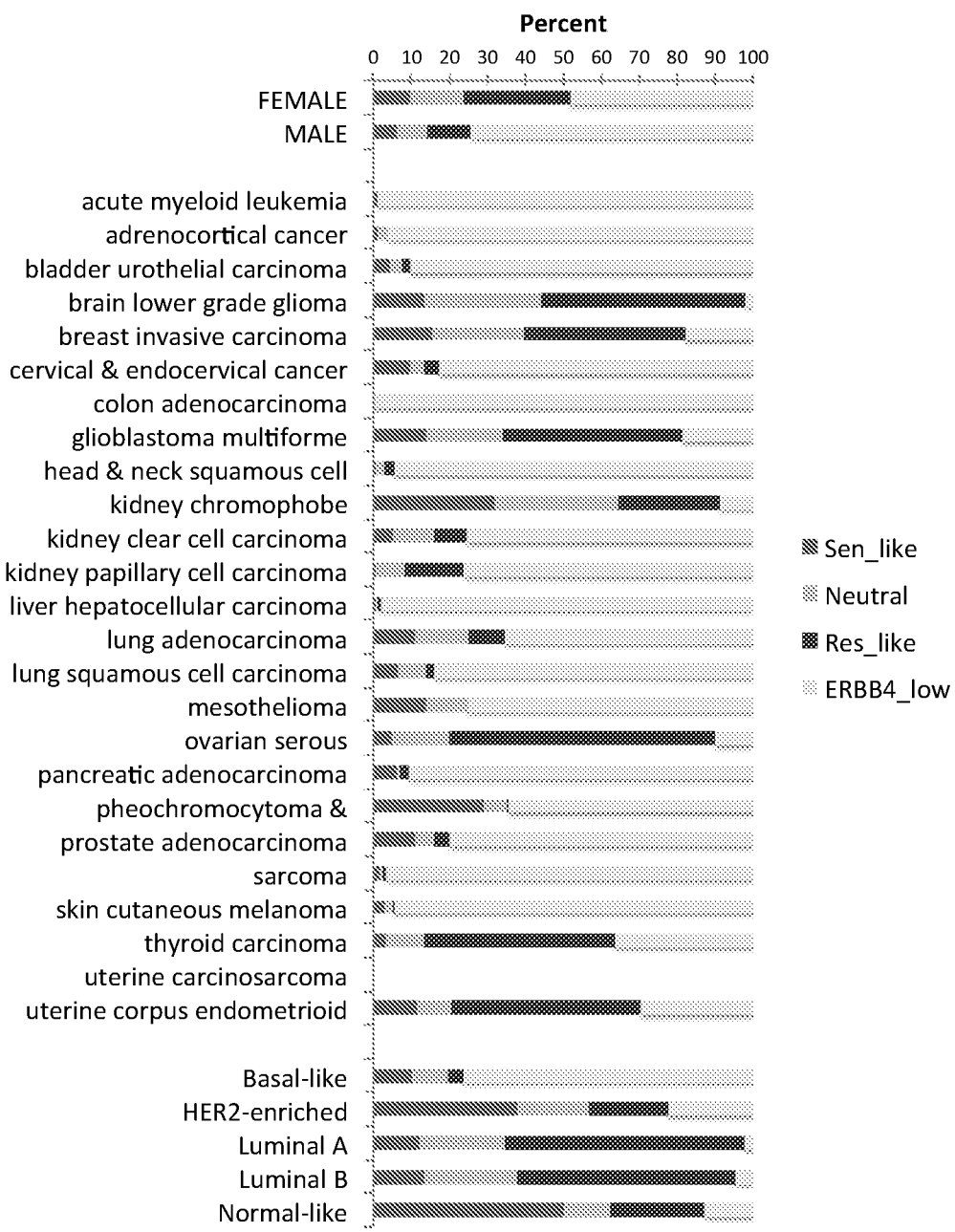
FIG. 8. Predicted ibrutinib responsiveness profiles of TCGA cancer samples based on DKK1/WNT5A ratio.

In order to identify cancer types and patient groups that may response to ibrutinib, we downloaded the TCGA (the Cancer Genome Atlas) RNA-Seq data on 25 different cancer types. With a cutoff of 1.0 FPKM (fragment per kilobase and million reads), among the total of 8,281 tumor samples, 3,292 samples expressed higher levels of ERBB4. FIG. 8 shows that about 50% of female samples expressed ERBB4, while only 25% of male samples did. By the cancer types, large fractions (60 to 98%) of samples from brain, breast, kidney, ovarian, thyroid, and uterine cancers showed higher levels of ERBB4 expression.

The DKK1/WNT5A signature was then applied to classify the ERBB4-positive samples into ibrutinib-sensitive-like (DKK1/WNT5SA>=2.0), ibrutinib-resistant-like (DKK1/WNT5A<=0.5), and neutral (0.5 <DKK1/WNT5A<2.0) groups. More than 60% of chromophobe renal cell carcinoma displayed either ibrutinib-sensitive or neutral signatures, which may respond to ibrutinib, although this type of renal carcinoma is rare and less aggressive than other kidney cancers (PMID: 22044519). In contrast, ovarian cancer samples were mostly (90%) ERBB4-positive as recently reported (PMID: 24901400), but the majority had ibrutinib-resistant signatures. Among more prevalent cancer types, 35 to 45% of samples from low-grade glioma, GBM (glioblastoma multiforme), and breast carcinoma were classified to have either sensitive-like or neutral signatures and thus represent major therapeutic targets of ERBB4-based treatments. As breast cancers can be subdivided into subtypes with distinct gene expression patterns, we also examined whether individual subtypes might display different profiles of ERBB4 and DKK1/WNT5A signatures.

As shown in FIG. 8, only 20% of basal-like cancers expressed ERBB4, but the majority of ERBB4-positive samples were predicted to respond to ibrutinib. In contrast, 75 to 90% of other subtypes expressed ERBB4, and considerable fractions of HER2-enriched (57%), luminal A (35%), luminal B (38%), and normal-like (63%) subtypes were classified to have either ibrutinib-sensitive and neutral signatures. In our cell based assays we saw inhibition raging from 60-75% in the responsive cell lines.

Another ERBB4 inhibitor is AST1306. It is currently in clinical trial phase I, but the phase II trial will be focusing more in EGFR and ERBB2 positive tumors.

We expect conventional treatment protocols with Ibrutinib to be effective in ERBB4 positive/WNT overactive tumors because the $IC_{50}$ for ERBB4 is in the same range as BTK.

In another embodiment, the invention provides a Nucleic Acid Programmable Protein Array (NAPPA) suitable for use with protein-tyrosine kinases. By "array" we mean an arrangement of molecules, such as biological macromolecules including peptides or nucleic acid molecules or biological samples (such as tissue sections), in for example, a substrate. A "microarray" is an array that is miniaturized for microscopic examination for evaluation or analysis. Arrays are sometimes called DNA chips or biochips.

The array of molecules ("features") makes it possible to carry out a very large number of analyses on a single sample at one time. In certain example arrays, one or more molecules (such as an oligonucleotide probe) will occur on the array multiple times, such as, for example, to provide internal controls. The number of locations on the array can vary, for example from at least two, at least four, at least six, to at least 9, at least 10, at least 14, at least 15, at least 20, at least 30, at least 50, at least 75, at least 100, at least 150, at least 200, at least 300, at least 500, least 550, at least 600, at least 800, at least 1000, or more. In a particular example, an array includes 2-100 addressable locations, such as 4-20 addressable locations. In particular examples, an array consists essentially of oligonucleotide probes specific for ERBB4 nucleic acid molecules. Our array had more than 100 protein kinases printed in quadruplicate. Each spot has DNA for the gene of interest, but we perform a expression step to transform the DNA microarray into a protein microarray. The protein microarray is the one we use to probe against Ibrutinib (or any other kinase inhibitor). ERBB4 was one of the proteins inhibited by Ibrutinib, but the array was not made with only ERBB4 DNA.

In particular examples, an array includes nucleic acid molecules, such as oligonucleotide sequences that are at least 10-15 nucleotides in length, or about 10-40 nucleotides in length. Within an array, each arrayed sample is addressable, in that its location can be reliably and consistently determined within at least two dimensions of the array. The feature application location on an array can assume different shapes.

For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein microarrays are a powerful platform for the unbiased screening of thousands of proteins simultaneously. Both basic and clinical research had benefited from the protein microarray platforms in applications such as the identification of protein substrates, identification of interactions partners and protein profiling in patient samples, to name just a few. The production of protein microarrays can be achieved by the immobilization of plasmid coding for the genes of interest followed by the in-situ protein synthesis using a cell—free expression system. After the expression, the proteins are immobilized locally in the vicinity of its coding plasmid. The final array comprises thousands of distinct features, each displaying a single protein of interest. The best-documented system for the production of protein microarrays using this strategy is NAPPA (Nucleic acid programmable protein array), a methodology developed at the inventors (Nat Methods. 2008; Curr Protoc Protein Sci. 2011.).

Prior to use of NAPPA arrays for the study of kinase inhibitor, an extensive optimization was performed to assure kinase activity with easily detectable signal. Every step of the microarray production was analyzed and optimized. First, the traditional chemistry used on NAPPA arrays was altered to decrease the levels of background signal. One of the main background sources in kinase assays performed in NAPPA was BSA (Bovine serum albumin), used to provide the correct viscosity for the printing mix. The highly phosphorylation levels of BSA decrease the dynamic range of the platform and new polymers were tested to replace BSA. A total of four different polymers with 10 distinct concentrations each were tested and the polymer with best performance was poly-lysine. Next, we optimized the expression system to increase the amount of protein displayed in each feature and to provide a human-based environment for protein folding, increasing the likelihood of proper folding and consequently the protein activity.

The new expression system uses a human cell- free expression system (such as 1-Step Coupled Human In Vitro Protein Expression), which showed an increase of more than 10 fold compared to the previously used system. Finally, the detection of the phosphorylation signal was optimized. More and a dozen of distinct pan antibodies against phospho-serines, phospho-threonines and/or phospho-tyrosines were tested in a set of ten distinct buffers (distinct salts, blocking agents, concentration of blocking agents) and the best condition was the antibody pan phospho-tyrosine p-100 in a TBST buffer with 3% BSA.

NAPPA kinase microarrays we generated with virtually all protein-tyrosine kinases from the human genome. The coding sequence for each tyrosine kinase was clone into an expression plasmid and immobilized on the microarray surface, with one protein kinase per feature. After the microarray was expressed, any phosphorylation that occurred during the expression step was removed by a treatment with lambda phosphatase.

Unphosphorylated microarrays were then incubated with a kinase buffer (25 mM Tris-HCl (pH 7.5), 5 mM beta-glycerophosphate, 2 mM dithiothreitol (DTT), 0.1 mM Na3VO4, 10 mM MgCl2) supplemented with 200 mM ATP and/or kinase inhibitors (concentration ranging from 0-10 uM). The kinase autophosphorylation activity was measured through the levels of phosphorylation present in each feature and was detected by phospho-tyrosine antibody. Phosphorylation levels observed in the absence of kinase inhibitor was considered 100% and the inhibition levels were calculated individually for each kinase and kinase inhibitor pair. Among the inhibitors tested on NAPPA kinase arrays were staurosporine, desatinib, imatinib and ibrutinib. Staurosporine is a pan kinase inhibitor used as a control.

Figure 9:
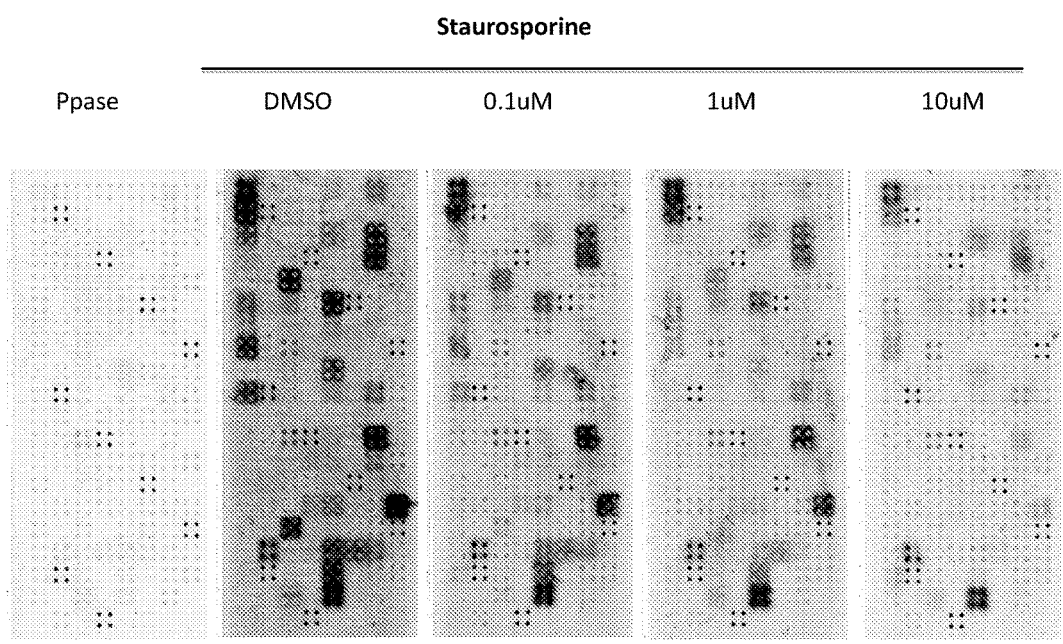
FIG. 9. Phosphorylation levels of kinase NAPPA arrays treated with Staurosporin during the autophosphorylation reaction.
Figures 10A, 10B:
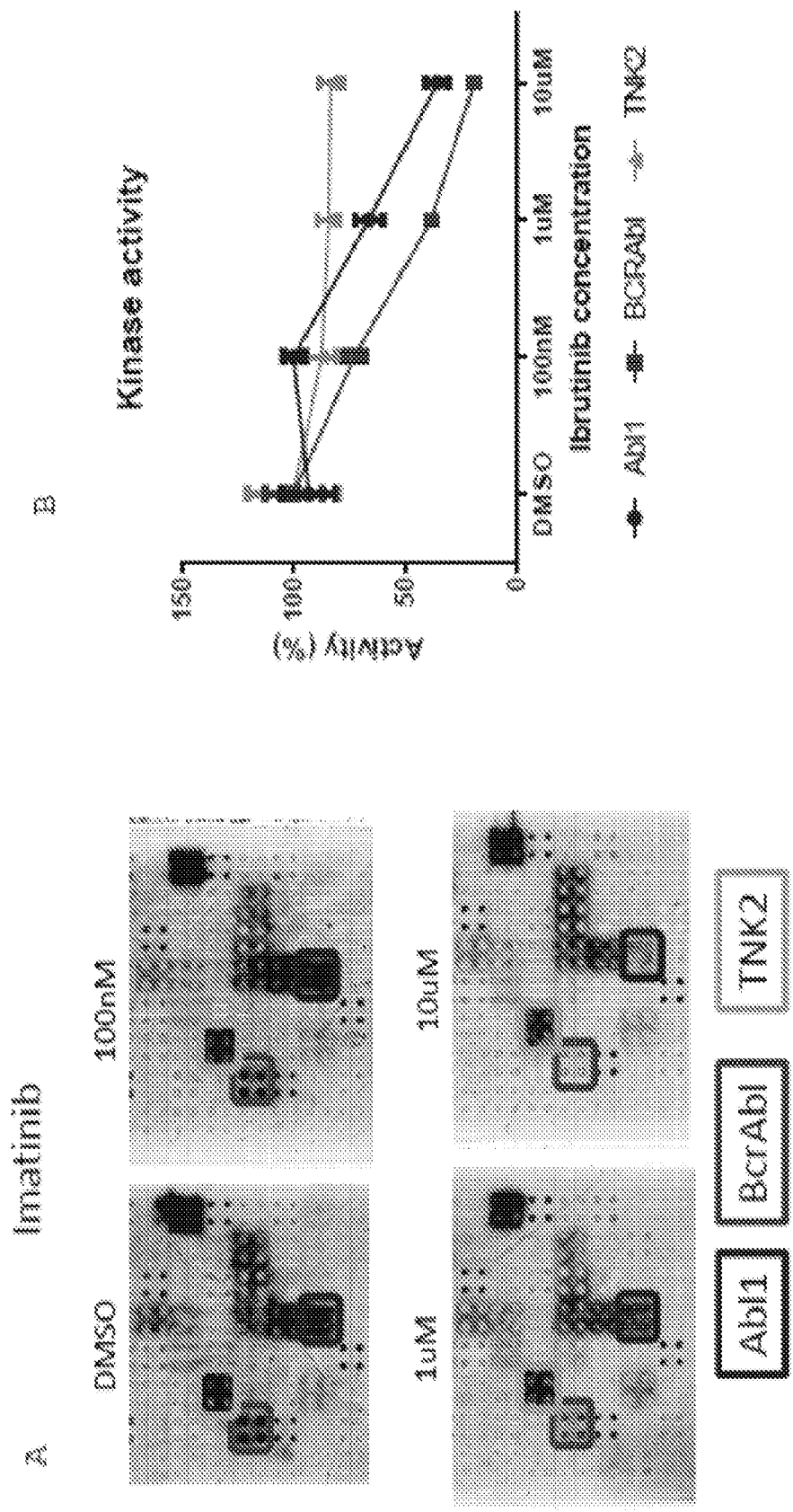
FIGS. 10A-10B. Phosphorylation levels of kinase NAPPA arrays treated with Imatinib during the autophosphorylation reaction.
Figures 11A, 11B, 11C:
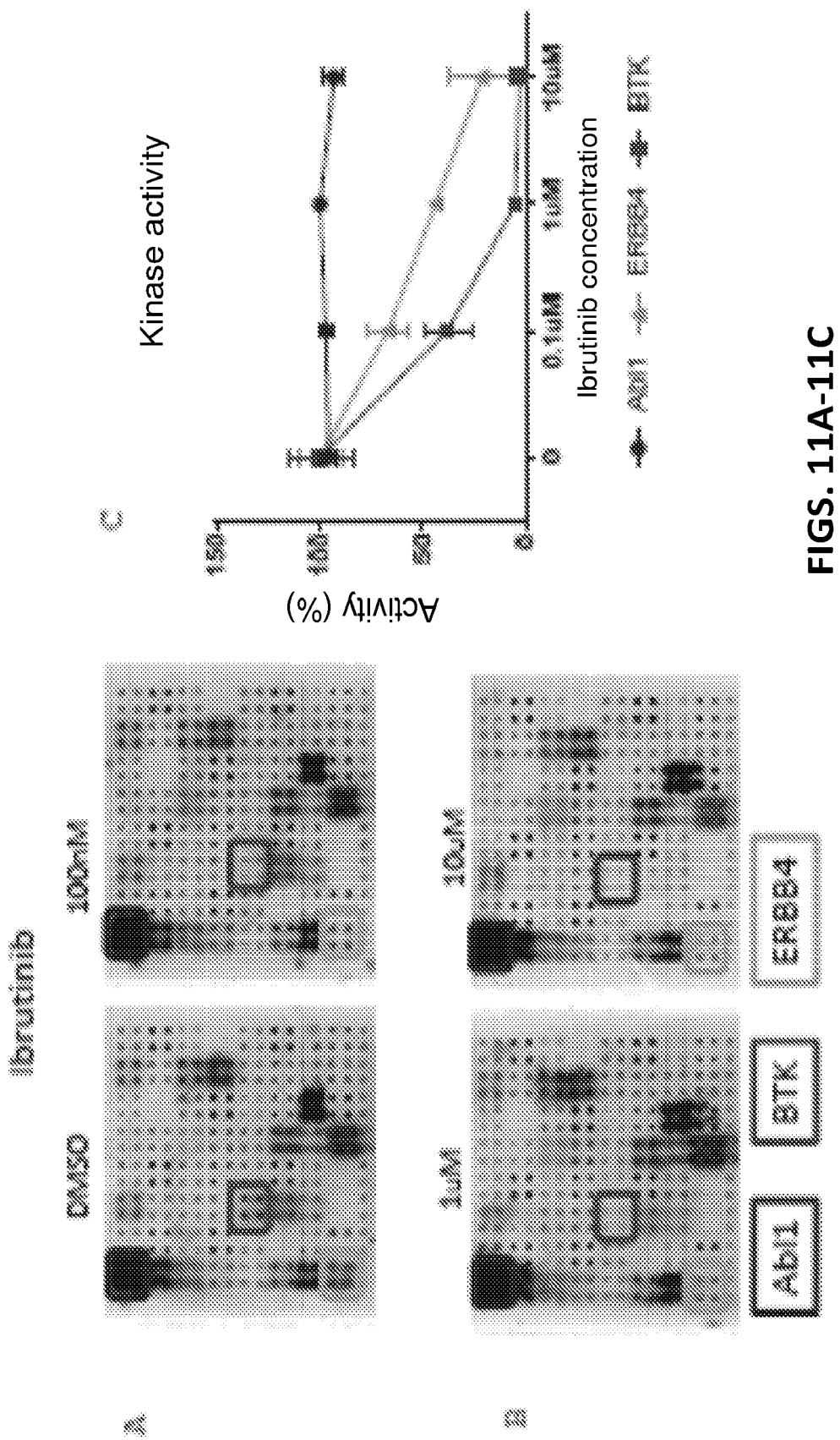
FIGS. 11A-11C. Phosphorylation levels of kinase NAPPA arrays treated with Ibrutinib during the autophosphorylation reaction.

As expected, the overall phosphorylation signal of the microarrays exposed to Staurosporine was drastically reduce when compared to the control slides, showing that NAPPA can be used for the test of kinase inhibitors (FIG. 9). Imatinib, Abl1 kinase inhibitor, was used to test if NAPPA was sensitive to detect selective inhibition. NAPPA kinase microarrays showed a significant reduction in Abl1 activity, while the other kinases remained mostly unaffected (FIG. 10). Ibrutinib was the last drug tested and among the kinases that were inhibited by this drug is BTK (canonical target) and ERBB4 (new target) (FIG. 11).

The inventors have now shown that NAPPA protein microarrays can be successfully adapted for the screening of kinases inhibitors. The arrays were optimized to provide low background signal during the kinase assay, allowing the kinase activity to be measured in the presence/absence of drugs. Drug-response curves were successfully obtained and the microarray data correlates with classical solution-based and bead-based kinase assays.

Once the NAPPA was optimized for the kinase inhibitor screening, several drugs were tested, including ibrutinib. Other potential targets include any kinase with inhibition greater than 50% on the microarray data and without any independent validation assay.

The NAPPA platform was successfully adapted and optimized to screen kinase inhibitors in a high-throughput and in an unbiased fashion. The greatest advantage of NAPPA over other platforms is the capability to screening kinases that harbor mutations to study drug resistance/selectivity. Since NAPPA uses plasmid DNA as the starting material for the generation of the protein microarrays, a simple site-direct mutagenesis can be used to create kinases with any mutation of interest. The number/type of mutations that can be tested is virtually unlimited.

Preferably, the methods provided herein are performed for a subject that has been diagnosed with cancer or other disorder associated with over-activation of ERBB4 signal transduction. As used herein, the term "cancer" refers to the broad class of disorders characterized by hyperproliferative cell growth, either in vitro (e.g., transformed cells) or in vivo. Cancers appropriate for treatment with ERBB4 inhibitor therapy include without limitation a variety of neoplasms, including benign or malignant tumors, a variety of hyperplasias, and the like. Non-limiting examples of cancers that can be diagnosed, monitored, prevented, and/or treated with a method of the invention can include: breast cancer, lung cancer, endometrial cancer, melanoma, colon cancer, gastric cancer, prostate cancer, ovarian cancer, glioma, and astrocytoma.

Any appropriate criteria can be used to confirm a subject's responsiveness to treatment by an ERBB4 inhibitor. For example, responsiveness to treatment by an ERBB4inhibitor is measured by at least one criterion selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel compounds and methods of the present invention are to be regarded as illustrative in nature and not restrictive.

EXAMPLES

The invention will be more fully understood upon consideration of the following non-limiting Examples. The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Example 1

Preparing a NAPPA Array for Protein-Tyrosine Kinases

NAPPA arrays suitable for measuring the activity of protein kinases and evaluating the selectivity of kinase inhibitors were produced using a variation of the published protocol (Proteomics Clin Appl. 2013 June; 7(5-6):372-7.). Briefly, NAPPA printing mix was prepared with plasmid DNA coding for genes of interest, anti-flag antibody, crosslinker and poly-lysine. Samples were agitated for 90 minutes at 1200 rpm at RT and printed in quadruplicate in aminopropyltriethoxysilane coated glass slides.

Arrays were stored in an airtight container at room temperature until use. NAPPA arrays were expressed using 1-Step Human Coupled IVT (Human IVTT). Slides were blocked in SuperBlock for 1 hour and dried with filtered air. HybriWells were applied on the top of the slide and 160 ul of Human IVTT, prepared according to the manufacturers' instructions, was added. Slides were incubated for 90 minutes at 30° C. and 30 minutes at 15° C., followed by one hour of blocking/washing with TBSTB (1× Tris-Buffered Saline supplemented with 0.2% Tween-20 and 3% BSA). The levels of protein expression were assayed with anti-Flag antibody followed by secondary antibodies labeled with cy3.

For the kinase assay, after the slides were expressed and blocked with TBSTB, the phosphatase treatment reaction was carried out for 1 hour to remove any phosphorylation that occurred during the protein expression.

Next, slides were washed with TBST to remove the phosphatase and the kinase reaction was initiated with kinase buffer with ATP in the presence or absence of drug. The kinase activity on the array was measured with antiphosphotyrosine antibody followed by secondary antibodies labeled with cy3. All antibodies incubations were performed in a 1:1000 dilution in TBSTB at RT, with agitation for one hour. Slide images were obtained with PowerScanner and the signal intensity was quantified using the Array-ProAnalyzer 6.3, using the default settings. The median intensity across the quadruplicates was measured and the background was corrected through the subtraction of the median value of the negative controls.

Based on these results, a number of cancer cell lines with high levels of ERBB4 (and low levels of BTK) were identified based on published RNA expression data including: H716 (large intestine), KLE (endometrium), H661 (lung), H522 (lung), OVKATE (ovary), OVSAHO (ovary), HEC59 (endometrium), COV434 (ovary), 1321N1 (brain), COV318 (ovary) and H146 (lung). BTK is the canonical target for Ibrutinib and the co-expression of ERBB4 and BTK in the same cell line would make it difficult to identify how Ibrutinib is blocking cell proliferation, if it is through BTK or ERBB4.

We obtained these cells lines from publicly available commercial sources such as ATCC, Sigma, AddexBio and JCRB (Japanese Collection of Research Bioresources) and treated them with Ibrutinib (0, 1 nM, 10 nM, 100 nM, 1 uM or 10 uM) for 7 days. Only ibrutinib was tested and we found four cell lines that were very sensitive (H716, KLE, H661, H522) and four lines that were apparently resistant (1321N1, Hec59, COV318, H416). This echoes what is often seen in patients, where some respond to a drug and some do not. It is therefore be useful to have a test that would predict which patients are the most likely to respond. To assess this, we set out to compare the gene expression in the responder cell lines with that in the resistant lines.

Cell lines obtained commercially were treated with ibrutinib (0 uM-10 uM) for up to 7 days and the number of live cells was counted with Titer Glow and/or trypan blue. RNA from ERBB4-sensitive and ERBB4-resistant cell lines was obtained with RNA easy (Quiagen) and the samples were sequenced using Illumina HiSeq2000. RNA-Seq data was analyzed and only proper genes (i.e. excluding anti-sense RNA, pseudo-genes, etc.) with FPKM higher than 1 in any of the 8 samples tested (4 sensitive and 4 resistant cell lines) were used for the classification. Using as cut off a fold change of 1.5 and P value <0.05 in two-tailed Mann-Whitney, a set of 400 distinct genes was obtained. This detailed list of genes that show differences between responsive and non-responsive cell lines is shown in FIG. 1.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

We claim:

1. A method of treating cancer in a subject in need thereof, the method comprising administering a therapeutically effective amount of an ERBB4 inhibitor to a subject having ERBB4 overexpressing cancer cells, wherein the ERBB4 overexpressing cancer cells are negative for expression of Bruton's tyrosine kinase (BTK), whereby the ERBB4-overexpressing/BTK-negative cancer cells are treated.

2. The method of claim 1, wherein the ERBB4 inhibitor is ibrutinib.

3. The method of claim 1, wherein the ERBB4 inhibitor is AST1306.

4. The method of claim 1, wherein the cancer is selected from the group consisting of breast cancer, lung cancer, endometrial cancer, melanoma, colon cancer, gastric cancer, prostate cancer, ovarian cancer, glioma, and astrocytoma.

5. The method of claim 1, wherein said subject is human.

6. A method for identifying and treating a patient disposed to respond favorably to an ERBB4 inhibitor therapy, the method comprising: (a) detecting ERBB4 overexpression in cancer cells in tissue sample from the patient, wherein the ERBB4 overexpressing cancer cells are negative for expression of Bruton's tyrosine kinase (BTK); (b) assessing levels of DKK1 and Wnt5A levels in the ERBB4-overexpressing/BTK-negative cancer cells, wherein a positive ratio of DKK1 to Wnt5A in a cancer cell from said sample indicates that the patient will benefit from ERBB64 inhibitor therapy; and (c) treating the patient with an ERBB4 in an amount effective to treat the cancer.

7. The method of claim 6, wherein the ERBB4 inhibitor is ibrutinib.

8. The method of claim 6, wherein the ERBB4 inhibitor is AST1306.

9. The method of claim 6, wherein said patient is a human patient.

* * * * *

UNITED STATES PATENT AND TRADEMARK OFFICE
CERTIFICATE OF CORRECTION

PATENT NO. : 10,045,990 B2
APPLICATION NO. : 15/555241
DATED : August 14, 2018
INVENTOR(S) : Fernanda Festa et al.

It is certified that error appears in the above-identified patent and that said Letters Patent is hereby corrected as shown below:

Column 12, Line 38, "WNT5SA" should be -- WNT5A --.

Column 18, Claim 6, Line 30, "ERBB64" should be -- ERBB4 --.

Signed and Sealed this
Second Day of October, 2018

Andrei Iancu
*Director of the United States Patent and Trademark Office*